United States Patent
Comes Franchini

(10) Patent No.: US 11,173,218 B2
(45) Date of Patent: Nov. 16, 2021

(54) BIOCOMPATIBLE POLYMERIC NANOPARTICLES CONTAINING FUNCTIONAL METAL NANOSTRUCTURES, PREPARATION PROCESSES, AND RELATED USES IN DIAGNOSTIC AND/OR THERAPEUTIC FIELDS

(71) Applicant: BIO-ON S.p.A., San Giorgio di Piano (IT)

(72) Inventor: Mauro Comes Franchini, San Giorgio di Piano (IT)

(73) Assignee: BIO-ON S.P.A., San Giorgio di Piano (IT)

(*) Notice: Subject to any disclaimer, the term of this patent is extended or adjusted under 35 U.S.C. 154(b) by 0 days.

(21) Appl. No.: 16/312,556

(22) PCT Filed: Jun. 27, 2017

(86) PCT No.: PCT/IB2017/053834
§ 371 (c)(1),
(2) Date: Dec. 21, 2018

(87) PCT Pub. No.: WO2018/002823
PCT Pub. Date: Jan. 4, 2018

(65) Prior Publication Data
US 2019/0224345 A1    Jul. 25, 2019

(30) Foreign Application Priority Data
Jun. 29, 2016   (IT) .................. 102016000067620

(51) Int. Cl.
*A61K 9/00*      (2006.01)
*A61K 49/18*     (2006.01)
(Continued)

(52) U.S. Cl.
CPC ...... *A61K 49/1857* (2013.01); *A61K 47/6935* (2017.08); *A61K 49/1824* (2013.01);
(Continued)

(58) Field of Classification Search
CPC .................................................. A61K 49/1857
See application file for complete search history.

(56) References Cited

U.S. PATENT DOCUMENTS 6,662,040 B1 * 12/2003 Henrichs ............... A61K 41/00
424/9.2
8,956,835 B2   2/2015 Nakas et al.

FOREIGN PATENT DOCUMENTS

CN    105012971 A    11/2015
WO    1999/023146 A1  5/1999
(Continued)

OTHER PUBLICATIONS

Li et al, Poly(ε-caprolactone)-Grafted Fe3O4 Nanoparticles: Preparation and Superparamagnetic Nanocomposites with Epoxy Thermosets, Ind. Chem. Res, 2015, 54, 171-180.*
(Continued)

*Primary Examiner* — Paul W Dickinson
(74) *Attorney, Agent, or Firm* — MH2 Technology Law Group LLP

(57) ABSTRACT

Biocompatible polymeric nanoparticles may include: a biocompatible polymer and/or functional metal nanostructures. The biocompatible polymer may be a polyhydroxyalkanoate (PHA). The functional metal nanostructures may include at least one noble metal, at least one magnetic metal oxide, or mixtures thereof. The biocompatible polymeric nanoparticles may have an average size less than or equal to 200 nanometers (nm).

20 Claims, 4 Drawing Sheets

Figure 1:
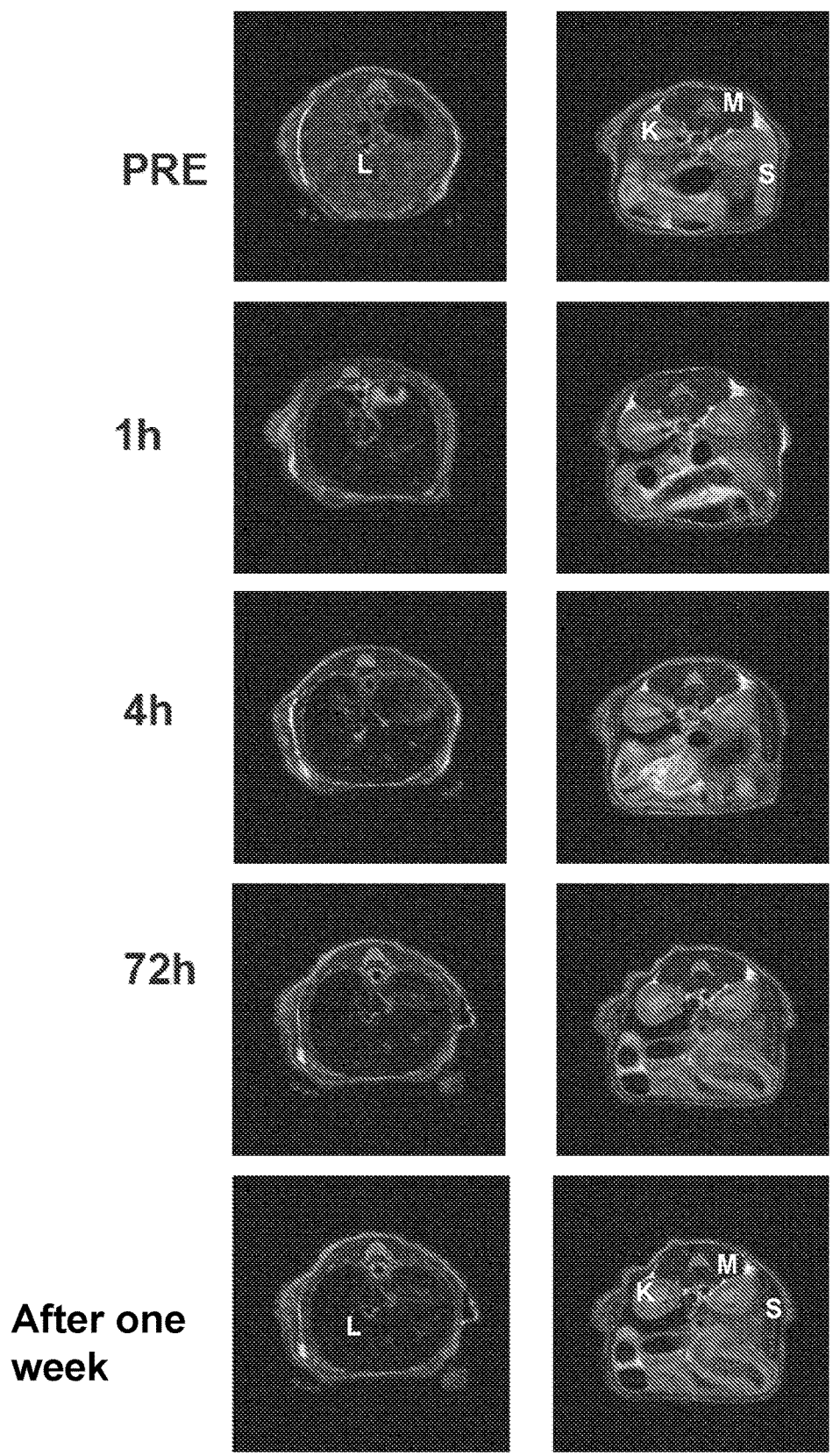

(51) Int. Cl.
  *A61K 49/22* (2006.01)
  *A61K 47/69* (2017.01)
  *A61P 35/00* (2006.01)
  *B82Y 5/00* (2011.01)
  *B82Y 40/00* (2011.01)

(52) U.S. Cl.
  CPC ............ *A61K 49/225* (2013.01); *A61P 35/00* (2018.01); *B82Y 5/00* (2013.01); *B82Y 40/00* (2013.01)

(56) References Cited

FOREIGN PATENT DOCUMENTS

| WO | 2011/045625 A1 | 4/2011 |
|----|----------------|--------|
| WO | 2015/015315 A2 | 2/2015 |
| WO | 2015/104664 A1 | 7/2015 |

OTHER PUBLICATIONS

Baldi et al., "In vivo anticancer evaluation of the hyperthermic efficacy of anti-human epidermal growth factor receptor-targeted PEG-based nanocarrier containing magnetic nanoparticles," International Journal of Nanomedicine, Jun. 24, 2014, pp. 3037-3056.

Gentili et al., "Double phase transfer of gold nanorods for surface functionalization and entrapment into PEG-based nanocarriers," The Royal Society of Chemistry, Chem. Commun., 2009, pp. 5874-5876.

Nikoobakht et al., "Preparation and Growth Mechanism of Gold Nanorods (NRs) Using Seed-Mediated Growth Method," Chem. Mater., Apr. 17, 2003, 15, pp. 1957-1962.

Sun et al., "Monodisperse MFe2O4 (M = Fe, Co, Mn) Nanoparticles," JACS Articles, J. Am. Chem. Soc., 2004, 126, 1, pp. 273-279.

Woo et al., "Easy Synthesis and Magnetic Properties of Iron Oxide Nanoparticles," Chem. Mater., 2004, 16, pp. 2814-2818.

Chu et al., "Surface deformation of gold nanorod-loaded poly(DL-lactide-co-glycolide) nanoparticles after near infrared irradiation: an active and controllable drug release system," Journal of Materials Chemistry, vol. 20, No. 16, pp. 3260-3264 (Jan. 1, 2010).

Errico et al., "Poly(hydroxyalkanoates)-Based Polymeric Nanoparticles for Drug Delivery," Journal of Biomedicine and Biotechnology, vol. 2009, pp. 1-10 (Jan. 1, 2009).

Solar et al., "Multifunctional polymeric nanoparticles doubly loaded with SPION and ceftiofur retain their physical and biological properties," Journal of Nanobiotechnology, vol. 13, No. 1, 12 pages (Feb. 13, 2015).

Song et al., "Ultrasmall Gold Nanorod Vesicles with Enhanced Tumor Accumulation and Fast Excretion from the Body for Cancer Therapy," Advanced Materials, vol. 27, No. 33, pp. 4910-4917 (Sep. 21, 2015).

Wang et al., "PLGA/PFC Particles Loaded with Gold Nanoparticles as Dual Contrast Agents for Photoacoustic and Ultrasound Imaging," Proc. of SPIE, vol. 8943, pp. 89433M-1 to 89433M-7 (Mar. 3, 2014).

A. Schleifenbaum (Authorized Officer), International Search Report and Written Opinion dated Nov. 15, 2017, International Application No. PCT/162017/053834, pp. 1-10.

* cited by examiner

BIOCOMPATIBLE POLYMERIC NANOPARTICLES CONTAINING FUNCTIONAL METAL NANOSTRUCTURES, PREPARATION PROCESSES, AND RELATED USES IN DIAGNOSTIC AND/OR THERAPEUTIC FIELDS

CROSS-REFERENCE TO RELATED APPLICATION(S)

This application is a national stage entry from International Application No. PCT/IB2017/053834, filed on Jun. 27, 2017, in the Receiving Office ("RO/IB") of the International Bureau of the World Intellectual Property Organization ("WIPO"), published as International Publication No. WO 2018/002823 A1 on Jan. 4, 2018; International Application No. PCT/IB2017/053834 claims priority under 35 U.S.C. § 119 from Italian Patent Application No. 102016000067620, filed on Jun. 29, 2016, in the Italian Patent and Trademark Office ("IPTO"), the entire contents of all of which are incorporated herein by reference.

The present invention relates to biocompatible polymeric nanoparticles containing functional metal nanostructures, their preparation process and relative use in the diagnostic and/or therapeutic field.

In the medical field, and in particular in the field of oncology, the need for non-invasive systems that simultaneously exert a diagnostic function and a therapeutic function, is strongly felt. These systems are commonly called "theranostic agents". As theranostic agents are electively localized in diseased tissues, they allow a more precise diagnosis of the disease and also the controlled release of active principles. In this respect, reference should be made, for example, to the article of D. Gentili et al, *Chem. Commun.*, 2009, 5874-5876, in which a double phase-transfer process is described for the preparation of nanostructures based on a polyethyleneglycol copolymer (PLGA-b-PEG-COOH) containing gold nanorods (GNRs).

GNRs are functional cylindrical nanostructures that have aroused great interest in the medical field as they have two distinct plasmon resonance bands: one due to the oscillations of the electrons on the transverse axis of the rod, which falls at around 520 nm, the other instead due to the oscillations of the electrons on the longitudinal axis, which, on the other hand, falls at higher wavelengths, around 700 nm. On increasing the aspect ratio (length/width ratio) of the rods, the wavelength relating to the longitudinal oscillation of the electrons can be moved towards even higher values (800-1200 nm) until the near IR (NIR=near infrared window) area is reached: in this way, it overlaps with the so-called "biological window" in which there is minimal absorption of light radiation by water, hemoglobin and hence by the tissues of human body, thus opening up wide possibilities of use for GNRs in the clinical biomedical field.

Thanks to the numerous optical instrumental methods, GNRs can be visualized inside the cells and act as contrast agents in the diagnostic imaging field. In particular, GNRs have ideal characteristics for photo-acoustic imaging applications and at the same time, if irradiated by a laser with their specific localized surface plasmon resonance (LSPR) frequency, thanks to the percentage of absorbed light which is rapidly transferred in the form of heat, the thermoablation of the tissues in which they are located can be obtained by selective burning, thus proving to be therapeutic.

Other functional metal nanostructures of interest are magnetic iron oxide nanoparticles (magnetites or maghemites), widely used in biological applications as they satisfy the necessary biocompatibility characteristics. In particular, superparamagnetic iron oxide nanoparticles (SPIONs) are used as contrast means and therefore imaging agents in Magnetic Resonance Imaging (MRI) for the diagnosis of cancer. The magnetic nanoparticles can be injected directly into the body to reach the tumoral mass and heated by means of an alternating magnetic field. This technique, called "hyperthermia", is in the development phase and has aroused great interest in the therapeutic field, as it would allow the selective destruction of cancer cells. In this respect, reference should be made to the article of G. Baldi et al, *Intl. J. Nanomedicine*, 2014:9, 3037-3056.

In order to convey functional metal nanostructures in the human body, said nanostructures must be charged in a medium which is highly biocompatible, in order to avoid undesired systemic effects in the patient, and which, at the same time, allows significant quantities of nanostructures to be charged without altering their functional characteristics and favouring their interaction with the cells and/or tissues to which they are destined. Furthermore, in order not to lose the advantages associated with the dimension typical of nanotechnologies, the carrier must also be within suitable nanomeric dimensions (generally below 200 nm), so as to allow an effective release during the systemic circulation to reach the cells and/or tissues affected by the disease.

Finally, the polymeric nanoparticles must be stable over time, without causing significant aggregation and separation phenomena from the dispersing medium which can jeopardize their functionality and therefore effectiveness.

The Applicant has now found that functional metal nanostructures can be charged into nanoparticles of a polyhydroxyalkanoate (PHA), which has a high biocompatibility and acts as an effective carrier for functional metal nanostructures without altering the biofunctionality of the latter.

According to a first aspect, the present invention therefore relates to biocompatible polymeric nanoparticles comprising a biocompatible polymer and functional metal nanostructures, wherein:

the biocompatible polymer is a polyhydroxyalkanoate (PHA);

the functional metal nanostructures comprise at least one noble metal or at least one magnetic metal oxide, or mixtures thereof;

the biocompatible polymeric nanoparticles have an average size lower than or equal to 200 nm, preferably lower than or equal to 150 nm.

According to another aspect, the present invention relates to biocompatible polymeric nanoparticles as defined above, for use as contrast agents in diagnostic image analyses, particularly magnetic resonance imaging analysis or photo-acoustic analysis.

According to another aspect, the present invention relates to biocompatible polymeric nanoparticles as defined above, possibly associated with an active principle, for use in the treatment of forms of cancer.

Polyhydroxyalkanoates (PHAs) are polymers produced by microorganisms isolated from natural environments or also by genetically modified microorganisms, which act as carbon and energy reserves, and are accumulated by various types of bacteria under unfavourable growth conditions and in the presence of excess carbon source. PHAs are synthesized and accumulated by about 300 different microbial species, included in more than 90 Gram-positive and Gram-negative bacteria genera, such as, for example, *Bacillus, Rhodococcus, Rhodospirillum, Pseudomonas, Alcaligenes, Azotobacter, Rhizobium*. PHAs are stored in cells in the form of microgranules, whose size and number per cell varies in the different bacterial species.

PHAs are generally polymers containing repetitive units having formula:

$$—O—CHR_1—(CH_2)_n—CO—\quad (I)$$

wherein:

$R_1$ is selected from: —H, $C_1$-$C_{12}$ alkyls, $C_4$-$C_{16}$ cycloalkyls, $C_2$-$C_{12}$ alkenyls, possibly substituted with at least one group selected from: halogen (F, Cl, Br), —CN, —OH, —COOH, —OR, —COOR (R=$C_1$-$C_4$ alkyl, benzyl);

n is zero or an integer from 1 to 6, and is preferably 1 or 2.

$R_1$ is preferably methyl or ethyl, and n is 1 or 2.

PHAs can be either homopolymers or copolymers or terpolymers. In the case of copolymers or terpolymers, these can be composed of different repetitive units having formula (I), or at least one repetitive unit having formula (I) combined with at least one repetitive unit deriving from comonomers that are capable of copolymerizing with hydroxyalkanoates, for example lactones or lactams. In this latter case, the repetitive units having formula (I) are present in a quantity equal to at least 10% in moles with respect to the total moles of repetitive units.

Particularly preferred repetitive units having formula (I) are those deriving from: 3-hydroxybutyrate, 3-hydroxyvalerate, 3-hydroxyhexanoate, 3-hydroxyoctanoate, 3-hydroxyundec-10-enoate, 4-hydroxyvalerate.

PHAs can be divided into three groups, depending on the number of carbon atoms that form the monomeric unit: PHAscls (short chain length) are composed of monomeric units having from 3 to 5 carbon atoms, PHAmcls (medium chain length) are composed of monomeric units having from 6 to 15 carbon atoms, whereas PHAlcls (long chain length) are composed of monomeric units having more than 15 carbon atoms. PHAscls have a high degree of crystallinity, whereas PHAmcls and PHAlcls are elastomers with a low crystallinity and have a low melting point.

Particularly preferred PHAs are: poly-3-hydroxybutyrate (PHB), poly-3-hydroxyvalerate (PHV), poly-3-hydroxyhexanoate (PHH), poly-3-hydroxyoctanoate (PHO), poly(3-hydroxybutyrate-co-3-hydroxyvalerate) (PHBV), poly(3-hydroxybutyrate-co-3-hydroxyhexanoate) (PHBH), poly(3-hydroxybutyrate-co-4-hydroxybutyrate), poly(3-hydroxyoctanoate-co-3-hydroxyundec-10-enoate) (PHOU), poly(3-hydroxybutyrate-co-3-hydroxyvalerate-co-4-hydroxyvalerate (PHBVV), or mixtures thereof.

The PHAs preferably have a weight average molecular weight ($M_w$) ranging from 5,000 to 1,500,000 Da, more preferably from 100,000 to 1,000,000 Da. The weight average molecular weight can be determined according to known techniques, in particular by means of GPC (Gel Permeation Chromatography) analysis or DSC (Differential Scanning calorimetry) analysis.

As far as the production of PHAs is concerned, this is preferably obtained by microbial fermentation of an organic substrate (for example, carbohydrates or other fermentable substrates, such as glycerol) by means of a strain of microorganisms capable of producing PHAs, and the subsequent recovery of the PHAs from the cell mass. For further details, reference should be made, for example, to patent applications WO 99/23146, WO 2011/045625 and WO 2015/015315. Substrates suitable for the production of PHAs via fermentation can be obtained in particular from the processing of vegetables, for example juices, molasses, pulps from sugar beet processing, sugar cane. These substrates generally contain, in addition to sucrose and other carbohydrates, organic growth factors, nitrogen, phosphorous and/or other minerals useful as nutrients for cell growth. An alternative is glycerol, a low-cost organic carbon source, as it is a by-product of the production of biodiesel, which can possibly be used in admixture with levulinic acid (see for example patent U.S. Pat. No. 8,956,835 B2).

With respect to the functional metal nanostructures, these comprise at least one noble metal or at least one magnetic metal oxide. The noble metal is preferably gold (Au), whereas the magnetic metal oxide is preferably a ferromagnetic metal oxide, preferably magnetite ($Fe_3O_4$) or maghemite ($\gamma$-$Fe_2O_3$), possibly doped with at least one transition metal different from Fe, in particular Mn, Co, Zn.

The functional metal nanostructures can have different forms, in particular they can be in the form of nanospheres, nanorods, nanostars, nanowires, nanocages or nanoplatelets The average size of these functional nanostructures preferably ranges from 1 nm to 100 nm, more preferably from 3 to 80 nm.

The functional metal nanostructures are more preferably selected from: gold nanorods (GNRs) and magnetic nanoparticles, or mixtures thereof.

With respect to gold nanorods, they preferably have an average length ranging from 10 to 100 nm, more preferably from 30 to 80 nm, and an average width from 2 to 25 nm, more preferably from 5 to 15 nm.

The gold nanorods preferably have an aspect ratio, defined as ratio between length and width, ranging from 2 to 20, more preferably from 3 to 10.

The functional metal nanostructures that can be used in the present invention are generally products available on the market or they can be prepared according to known techniques. As far as the commercial products are concerned, reference should be made for example to the catalogues of the companies Nanopartz and Sigma-Aldrich.

The gold nanorods can be prepared, for example, by the use of rigid templates or with suitable surfactants (seed-assisted growth). In the former case, inorganic materials (in particular oxides) are used as templates, or polymeric materials having pores with a substantially cylindrical form, in which the nanorods are grown by deposition of the metal. In the latter case, the nanorods are grown in an aqueous or non-aqueous medium in the presence of a suitable surfactant, in particular hexadecyltrimethylammonium bromide (CTAB) in an aqueous environment, or trioctylphosphine oxide in a non-aqueous environment. For further details, reference should be made, for example, to the article of B. Nikoobakht et al, *Chem. Mater.*, 2003, 15, 1957-1962, or the above-mentioned article of D. Gentili et al, *Chem. Commun.*, 2009, 5874-5876.

With respect to magnetic nanostructures, these are generally in the form of substantially spherical nanoparticles, composed of magnetite ($Fe_3O_4$) or maghemite ($\gamma$-$Fe_2O_3$), possibly doped with at least one transition metal different from Fe, in particular Mn, Co, Zn, more preferably Mn ($MnFe_2O_4$). They preferably have an average size ranging from 1 nm to 80 nm, more preferably from 10 nm to 50 nm.

The magnetic nanostructures can be prepared according to known techniques, for example by the thermal decomposition of metal carbonyls. Reference should be made, for instance, to the articles of K. Woo et al, *Chem. Mater.*, 2004, 16, 2814-2818, and S. Sun et al, *J. Am. Chem. Soc.*, 2004, 126(1), 273-279.

The dimensions of the nanoparticles and nanostructures defined above can be determined by means of known techniques, in particular by means of Dynamic Light Scattering (DLS), TEM (Transmission Electron Microscopy) image analysis, or also by means of ultraviolet-visible (UV-Vis) spectroscopy.

The functional metal nanostructures preferably have at least one hydrophobizing agent on the surface. Said agent has the function of increasing the compatibility between the metal nanostructures and the lipophilic part of the PHA nanoparticle, so as to favour the embedding of said nanostructures in the polymer itself. The most suitable hydrophobizing agent for exerting this function is mainly selected in relation to the type of metal nanostructure, since the hydrophobizing agent has a hydrocarbon chain, having a length sufficient for favouring interaction with the PHA, functionalized with at least one group which is capable of interacting with the surface of the metal nanostructures.

In the case of GNRs, for example, the hydrophobizing agent is preferably a thiol R—SH, wherein R is a hydrocarbon group, saturated or unsaturated, aliphatic and/or aromatic, having from 4 to 28 carbon atoms, possibly substituted by functional groups, such as ester, amide, carboxyl, hydroxide, amino groups.

In the case of magnetic nanostructures, the hydrophobizing agent is preferably selected from carboxylic acids, alcohols, polyols or long-chain amines (generally $C_8$-$C_{28}$), or derivatives thereof, for example oleic acid, oleic amine, derivatives of catechol, and carbohydrate derivatives.

The hydrophobizing agent can be added to the metal nanostructures when these have already been produced, or, it is preferably added to the medium in which the preparation of the nanostructures takes place.

The polymeric nanoparticles according to the present invention preferably comprise from 70% by weight to 99% by weight, more preferably from 80% by weight to 95% by weight, of polyhydroxyalkanoate (PHA), and from 1% by weight to 30% by weight, more preferably from 5% by weight to 20% by weight, of functional metal nanostructures, the percentages being calculated with respect to the overall weight of the nanoparticles.

In a preferred embodiment, the polymeric nanoparticles according to the present invention preferably also comprise at least one surfactant, more preferably a non-ionic surfactant. The presence of the surfactant improves the dispersion of the polymer nanoparticles in an aqueous medium, for example in a physiological solution, so as to obtain a stable suspension which can be administered to the patient, for example parenterally, in particular by means of intravenous injection. The quantity of said at least one surfactant may generally range from 1% by weight to 10% by weight, more preferably from 3% by weight to 6% by weight, the percentages being calculated with respect to the total weight of the nanoparticles.

The choice of the surfactant depends, in addition of course to its effectiveness in dispersing the nanoparticles in the aqueous medium, also on its biocompatibility, so as to avoid adverse reactions following parenteral administration.

The surfactant can be selected, for example, from:
polyethyleneglycol alkylethers;
polyethyleneglycol sorbitan alkylesters, for example polyethyleneglycol sorbitan monolaurate;
D-alpha-tocopherol polyethyleneglycol succinate;
polyvinylalcohol.

The surfactant is preferably added to the nanoparticles during their preparation, so as to obtain an effective integration within the nanoparticles themselves, as better illustrated hereunder.

The presence of functional metal nanostructures allows the use of the nanoparticles according to the present invention in techniques of diagnostic imaging by means of magnetic resonance (MRI—Magnetic Resonance Imaging) or through ultrasound-photoacoustic techniques. Furthermore, the nanoparticles according to the present invention can be used for therapeutic purposes for the removal or reduction of tumours by medical lasers which, in the presence of metal nanostructures, develop heat locally and allow the ablation of cancer cells.

In a preferred embodiment, the biocompatible polymeric nanoparticles according to the present invention can also comprise at least one active principle, which is conveyed by the nanoparticles so as to reach targeted cells affected by the disease to be treated. Said active principle is preferably an antitumour agent, such as, for example: doxorubicin, temozolamide, cis-platinum, carmustine, paclitaxel, and others.

According to a further aspect, the present invention relates to a process for the preparation of biocompatible polymeric nanoparticles as defined above, which comprises:
preparing an emulsion comprising: (a) a hydrophobic phase comprising a solution of PHA in at least one organic solvent in which the functional metal nanostructures are dispersed; (b) an aqueous phase; and (c) at least one surfactant;
subjecting said emulsion to an ultrasonic treatment (sonication);
evaporating said at least one organic solvent from said emulsion after sonication so as to obtain a suspension of the biocompatible polymeric nanoparticles which incorporate the metal nanostructures.

Organic solvents that can be used are those normally adopted for dissolving PHAs, for example: chloroform, dimethylsulfoxide, dichloromethane, methanol, ethanol, acetonitrile, N,N-dimethylformamide, or mixtures thereof.

As far as the surfactant is concerned, this can be selected from those indicated above for favouring the formation of stable suspensions of nanoparticles in an aqueous medium.

The ultrasound treatment (sonication) can be carried out according to known techniques, for example by means of a tip sonicator. Preferably, during the sonication step, the emulsion is maintained in an ice bath, so as to avoid a localized overheating of the same due to the action of the ultrasounds. It is believed that the sonication step allows the system to be emulsified so as to obtain the incorporation of the metal nanostructures inside the lipophilic part of the polymer nanoparticles, whereas the surfactant is located outside the nanoparticles, so as to favour the dispersion of the same in an aqueous medium.

At the end of the sonication step, the organic solvent is removed from the emulsion by evaporation, preferably vacuum evaporation so as to avoid heating the emulsion and therefore avert any possible degradations of the polymer and/or metal nanostructures.

According to another aspect, the present invention relates to a further process for the preparation of biocompatible polymeric nanoparticles as defined above, which comprises:
preparing a solution of PHA in at least one organic solvent;
preparing a suspension of the metal nanostructures in an aqueous medium in the presence of at least one surfactant;
putting the solution of PHA in contact with the suspension of metal nanostructures so as to obtain a suspension of biocompatible polymeric nanoparticles which incorporate the metal nanostructures.

This second process (which can be defined as a solvent deposition or nanoprecipitation process) has the advantage of being able to be effected continuously, also with large volumes, unlike the first process which comprises the sonication step, which is carried out batchwise on relatively reduced volumes. Also in this case, the surfactant can be selected from those indicated above.

The solution of PHAs can be put in contact with the suspension of metal nanostructures in a container where these are conveyed in continuous through peristaltic pumps. A suspension of biocompatible polymeric nanoparticles incorporating the metal nanostructures is removed from the container, preferably continuously.

In both of the processes described above, the suspension of nanoparticles thus obtained is preferably subjected to filtration, so as to separate the nanoparticles from the liquid phase in which they are suspended. The nanoparticles can then be subjected to purification, so as to eliminate any possible processing residues that can be undesirable for a systemic administration.

Alternatively, if the aqueous phase already has the desired characteristics for use, for example if a solution of saline buffer (pH=7) is used as aqueous phase, the suspension can be used as such, without having to filter the nanoparticles and re-suspend them.

The biocompatible polymeric nanoparticles obtained as described above can be administered to the patient in the form of a suspension in an aqueous medium, in particular in a physiological solution. Said suspension can be administered in particular parenterally, for example by intravenous injection.

Furthermore, the suspension of nanoparticles can be subjected to lyophilization, so as to obtain isolated nanoparticles, which can be easily dispersed in a physiological solution at the moment of use.

In a preferred embodiment, the functional metal nanostructures are composed of a mixture of gold nanorods and magnetic nanoparticles.

The contemporaneous presence of the two contrast agents offers a considerable advantage for diagnosis and therapy in the field of oncology, as they provide important and complementary characteristics. The presence of magnetic nanoparticles allows MRI (Magnetic Resonance Imaging) techniques to be used, which are extremely useful for pre-operative visualizations, generally with immediate interpretation, which give a first indication to the surgeon, but have the disadvantage of having a limited spatial resolution, especially on the edges of the tumoral mass. The presence of GNRs, on the contrary, also allows the use of a photo-acoustic imaging technique, which overcomes the problems of limited resolution and penetration depth, allowing a better visualization of the margins of the tumour. It can therefore be used during the operation for allowing the surgeon a precise and complete resection of the tumour mass.

The following embodiment examples are provided for purely illustrative purposes of the present invention and should not be considered as limiting the protection scope defined by the enclosed claims.

EXAMPLE 1

Preparation of PHB Nanoparticles Containing Gold Nanorods (GNRs).

25 mg of PHB (poly-3-hydroxybutyrate) were dissolved in 2.5 mL of chloroform. The solution was previously filtered on diatomaceous earth (Celite®) to remove the small insoluble aggregates. GNRs, rendered lipophilic thanks to the presence on the surface of ethyl-11-mercaptoundecanoate, as described in the article of D. Gentili et al. *Chem. Commun.*, 2009, 5874-5876, were then added to the above solution. The GNRs were also dispersed in chloroform (volume: 2.5 mL, concentration: 1.0 mM). The GNRs had the following dimensions: average length 50 nm, average width 12 nm, aspect ratio 4.16.

50 mL of aqueous solution containing polyethyleneglycol sorbitan monolaurate (Tween® 20-3.8 mg/mL) as surfactant were then added to the previous organic phase and the whole mixture was finally emulsified with a tip sonicator (600 W input, 50% ampl, 3 min, ice bath). The emulsion obtained was evaporated under vacuum until the chloroform had been completely removed, then purified and concentrated by centrifugation on specific membranes (Amicon Ultra, Ultracel membranes, 100,000 NMWL, Millipore, USA) washing three times with water. The final volume was adjusted to 2 mL with water.

Results

DLS (Dynamic Light Scattering) analysis showed the presence of nanoparticles having an average hydrodynamic diameter of about 115/130 nm, a good polydispersity index (PDI) equal to 0.150/0.170 and with negative Zeta surface potential (−39/−31.0 mV). The concentration of gold, estimated by atomic adsorption spectroscopy analysis (AAS) was equal to 0.75 mM.

EXAMPLE 2

Preparation of PHB Nanoparticles Containing nanoparticles of magnetite ($Fe_3O_4$).

The same procedure as Example 1 was followed, substituting the gold nanorods with an equal amount of nanoparticles of magnetite ($Fe_3O_4$) rendered lipophilic by the inclusion of oleic acid.

Results.

DLS (Dynamic Light Scattering) analysis showed the presence of nanoparticles having an average hydrodynamic diameter of about 139 nm, a good polydispersity index (PDI) equal to 0.150/0.200 and with negative Zeta surface potential (−25.2 mV).

The concentration of iron, estimated by atomic adsorption spectroscopy analysis (AAS) was equal to 3.16 mM.

EXAMPLE 3

Preparation of PHB Nanoparticles Containing Gold Nanorods (GNRs) and Magnetite Nanoparticles.

25 mg of PHB (poly-3-hydroxybutyrate) were dissolved in 2 mL of chloroform. The lipophilic GNRs of Example 1 (volume: 2 mL, concentration: 1.0 mM) were added to this solution, together with the lipophilic magnetite ($Fe_3O_4$) nanoparticles of Example 2 (volume: 2 mL, concentration: 1.0 mM) also dispersed in chloroform. 14 mL of ethanol were then added, thus obtaining a mixed organic solution of ethanol:chloroform 70:30.

50 mL of an aqueous solution containing the surfactant Tween® 20 (3.8 mg/mL) were then added to the previous organic phase and the while mixture was finally emulsified with a tip sonicator (600 W input, 50% ampl, 3 min, ice bath). The emulsion obtained was evaporated under vacuum until the complete removal of the ethanol and chloroform, then purified and concentrated by centrifugation on specific membranes ((Amicon Ultra, Ultracel membranes, 100,000 NMWL, Millipore, USA) washing three times with water. The final volume was adjusted to 2 mL with water. The solution obtained was finally filtered on syringe filters Sterivex®-GP 0.22 µm of polyethersulfone (Millipore, USA).

Results

DLS (Dynamic Light Scattering) analysis showed the presence of nanoparticles having an average hydrodynamic diameter of about 130/150 nm, a good polydispersity index (PDI) equal to 0.160/0.190 and with a negative surface potential Zeta (−40/−30 mV). The concentration of gold and iron, estimated by atomic adsorption spectroscopy analysis (AAS), was equal to 0.80 mM of gold and 2.55 mM of iron.

EXAMPLE 4

MRI Study of the Bio-Distribution of PHB+Magnetite ($Fe_3O_4$) Nanoparticles in Healthy Laboratory Mice.

The PHB nanoparticles embedding magnetite ($Fe_3O_4$) nanoparticles obtained according to what is described in Example 1, were injected intravenously in bolus with an injection rate of about 5 ml/min and an overall dosage of 1 mg Fe/kg, corresponding to an administered volume of 10.53 mL/kg. MRI acquisitions were effected at zero time (before the injection) and at 1, 4, 72 hours and one week after the injection.

The mice were anesthetized with isoflurane gas (2%) in 98% $O_2$. During the MRI acquisitions, the anaesthesia was maintained regulating the gas flow in relation to the breathing frequency of the mouse, the latter being maintained at a temperature of 37° C.

The MRI acquisitions were effected with an 1T MR scanner (Icon, Bruker). The weighed-T2 images were obtained with specific sequences, using the following parameters: TR=2000 ms, TE=50 ms, FA=180°, NEX=4, MTX=192×192, FOV 3.5 cm.

All the MRI images acquired were transferred to specific software for a quantitative analysis. The relative signal analysis intensity (SI) of the liver, spleen and kidneys, was estimated. This procedure was followed to provide an estimation of the total signal of the image, subtracting the background noise.

The average SI values of the organs [$rSI_{(organ)}$] were calculated according to the following equation:

$$rSI_{(organ)}=[SI_{(organ)}-SI_{(muscles)}]/[SI_{(organ)}+SI_{(muscle)}]$$

wherein $SI_{(organ)}$ is the average of the three intensity reduction values of the signal (ROI) on the organ under examination and $SI_{(muscles)}$ is the ROI of the paraspinal muscle.

The intensity reduction percentage of the signal (SIR) was then calculated by comparing the $rSI_{(organ)}$ values before and after the injection in order to evaluate the bio-distribution of the nanoparticles of PHB+magnetite.

Figure 2:
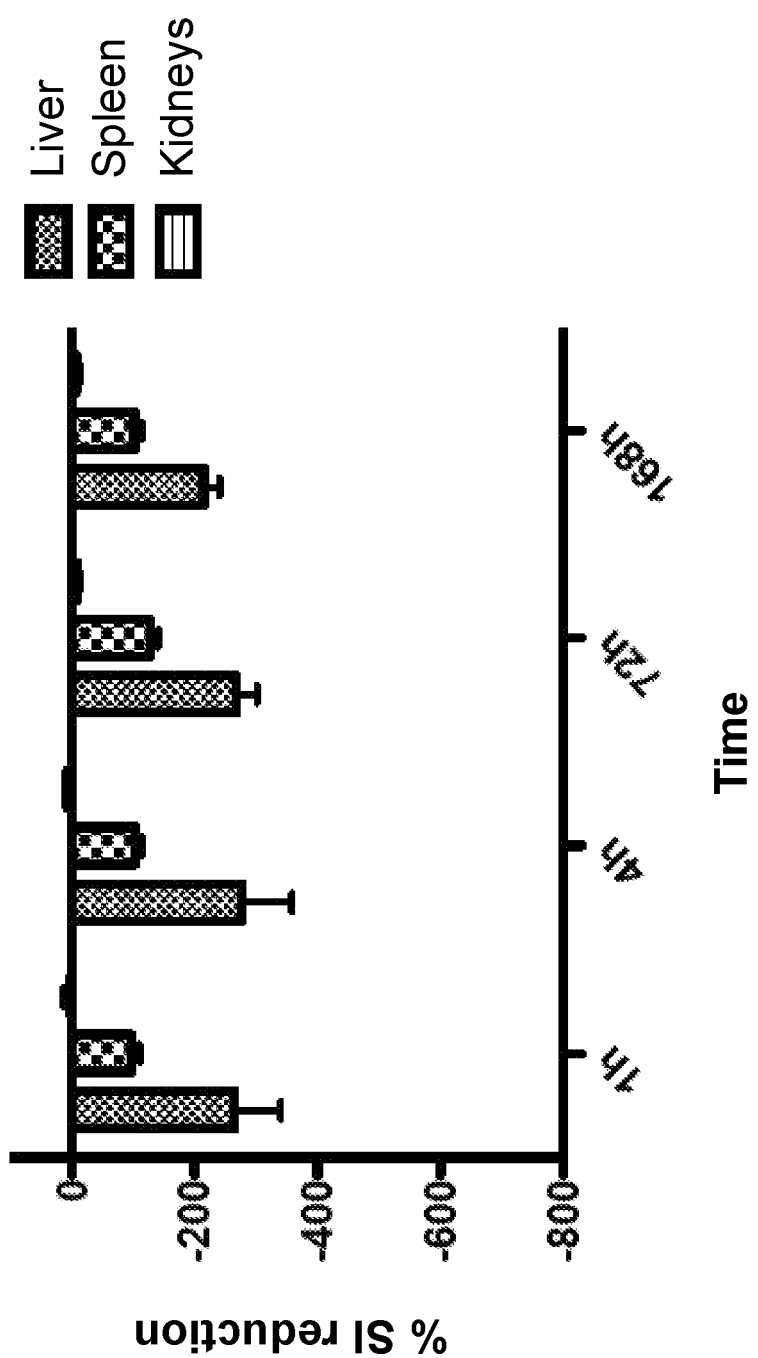

The MRI images are indicated in FIG. 1, whereas FIG. 2 is a graphic representation of the average of the SIR percentages due to the absorption of said nanoparticles in the various organs.

EXAMPLE 5

MRI Study of the Bio-Distribution of PHB+Manganese Ferrite ($MnFe_2O_4$) Nanoparticles in Healthy Laboratory Mice.

PHB nanoparticles englobing nanoparticles of manganese ferrite ($MnFe_2O_4$), obtained following the same procedure described in Example 1, were injected intravenously in bolus with an injection rate of about 5 ml/min and an overall dosage of 1 mgFe/kg, corresponding to an administered volume of 10.53 mL/kg. MRI acquisitions were effected at zero time (before the injection) and at 1, 4, 24 and 48 hours after the injection.

Figure 3:
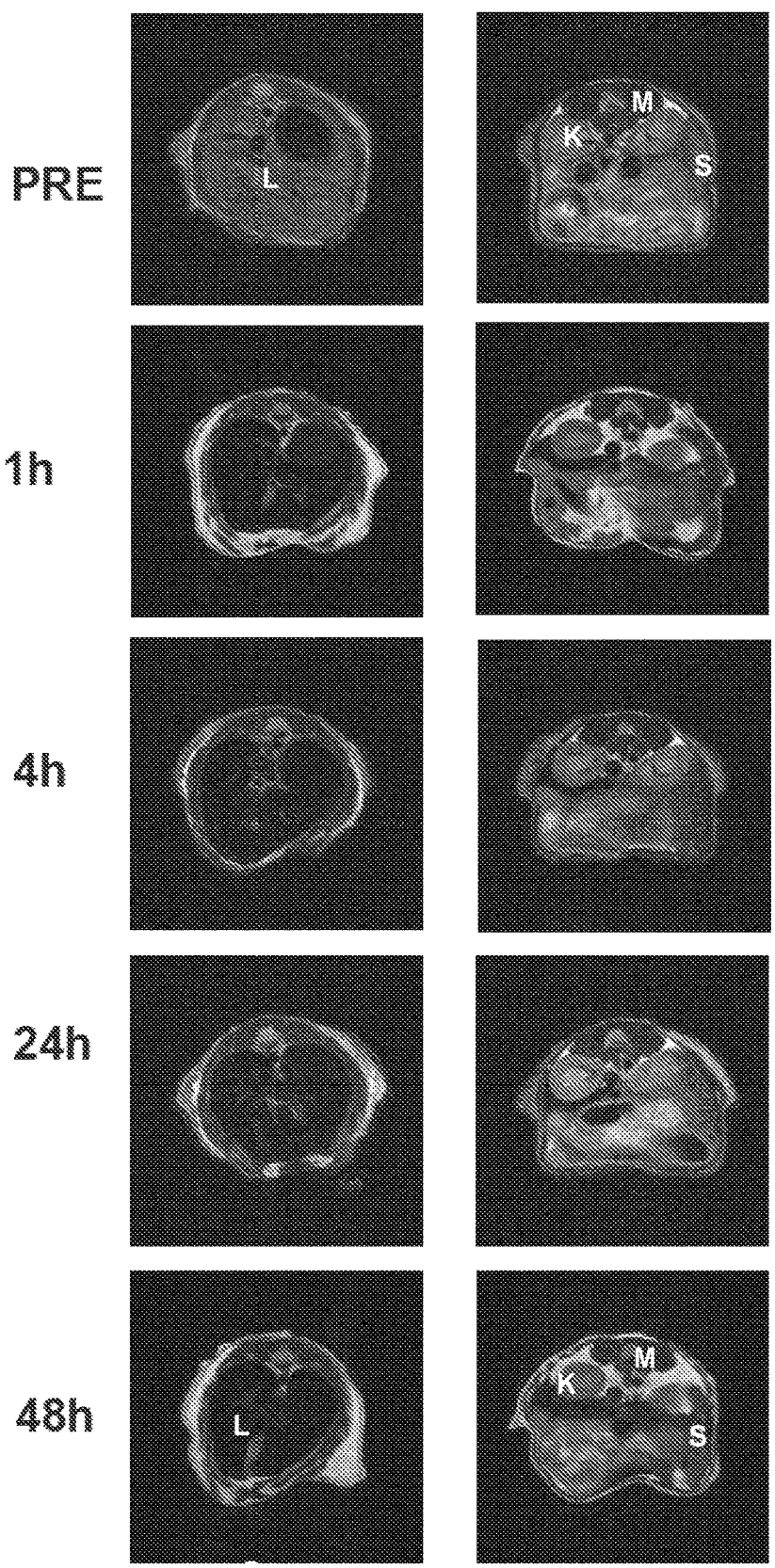
Figure 4:
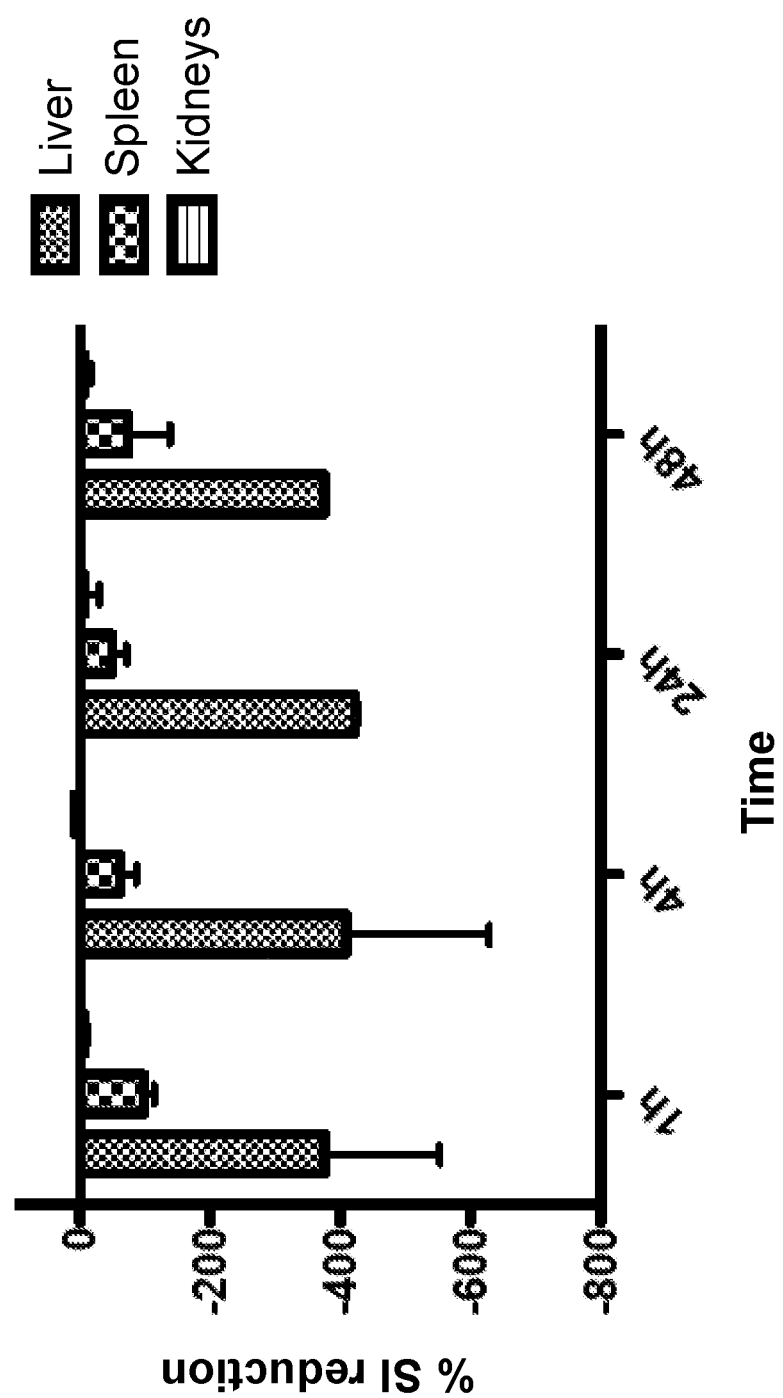

Following the same procedure described in Example 4, the MRI images were acquired and processed, and are shown in FIG. 3, whereas FIG. 4 graphically represents the average of the SIR percentages due to the absorption of said nanoparticles in the various organs.

From the results obtained in Examples 4 and 5 indicated above, the following can be observed:

(1) The quantitative evaluation of the SIR % shows the fast migration of the PHB nanoparticles containing magnetic contrast agent into the liver and spleen.

(2) One hour after the injection of PHB+$Fe_3O_4$ nanoparticles, the SIR % value shows a strong accumulation in the liver (264%) and in the spleen (97.6%). After a week, a significant permanence in the liver and spleen is observed.

(3) One hour after the injection of PHB+$MnFe_2O_3$ nanoparticles, the SIR % value shows a greater accumulation in the liver (376%) with respect to the PHB+$Fe_3O_4$ nanoparticles, whereas the accumulations in the spleen are substantially identical.

(4) No toxic effects deriving from the injection of PHB+$Fe_3O_4$ and PHB+$MnFe_2O_3$ into the mice at a dosage of 1 mgFe/Kg, were observed.

The invention claimed is:

1. Biocompatible polymeric nanoparticles, comprising:
a biocompatible polymer; and
functional metal nanostructures;
wherein the biocompatible polymer is a polyhydroxyalkanoate (PHA) containing repetitive units having formula (I):

—O—$CHR_1$—$(CH_2)_n$—CO—     (I), where $R_1$ is selected from: —H, $C_1$-$C_{12}$ alkyls, $C_4$-$C_{16}$ cycloalkyls, $C_2$-$C_{12}$ alkenyls, the $C_1$-$C_{12}$ alkyls, $C_4$-$C_{16}$ cycloalkyls, $C_2$-$C_{12}$ alkenyls being possibly substituted with at least one group selected from: F, Cl, Br, —CN, —OH, —COOH, —$OR_2$, —$COOR_2$, wherein $R_2$ is selected from $C_1$-$C_4$ alkyl and benzyl; and
where n is an integer from 1 to 6;
wherein the functional metal nanostructures comprise gold (Au) nanostructures,
wherein the functional metal nanostructures have on a surface at least one hydrophobizing agent, wherein the at least one hydrophobizing agent is a thiol $R_3$—SH, where $R_3$ is a hydrocarbon group, saturated or unsaturated, aliphatic and/or aromatic, having from 4 to 28 carbon atoms, and
wherein the biocompatible polymeric nanoparticles have an average size less than or equal to 200 nanometers (nm).

2. The biocompatible polymeric nanoparticles of claim 1, comprising:
greater than or equal to 70% by weight and less than or equal to 99% by weight of the PHA; and
greater than or equal to 1% by weight and less than or equal to 30% by weight of the functional metal nanostructures;
wherein the percentages are calculated with respect to a total weight of the biocompatible polymeric nanoparticles.

3. The biocompatible polymeric nanoparticles of claim 1, wherein the PHA has a weight average molecular weight ($M_w$) from 5,000 daltons (Da) to 1,500,000 Da.

4. The biocompatible polymeric nanoparticles of claim 1, wherein the functional metal nanostructures consist of gold (Au) nanostructures.

5. The biocompatible polymeric nanoparticles of claim 1, wherein the gold (Au) nanostructures are in a form of nanospheres, nanorods, nanostars, nanowires, nanocages, or nanoplatelets, having an average size greater than or equal to 1 nm and less than or equal to 100 nm.

6. The biocompatible polymeric nanoparticles of claim 5, wherein the gold (Au) nanostructures comprise gold nanorods.

7. The biocompatible polymeric nanoparticles of claim 6, wherein the gold nanorods have an average length greater than or equal to 10 nm and less than or equal to 100 nm, and an average width greater than or equal to 2 nm and less than or equal to 25 nm.

8. The biocompatible polymeric nanoparticles of claim 1, further comprising:
at least one surfactant.

9. The biocompatible polymeric nanoparticles of claim 8, wherein the at least one surfactant is present in an amount greater than or equal to 1% by weight and less than or equal to 10% by weight, and
wherein the percentages are measured with respect to a total weight of the biocompatible polymeric nanoparticles.

10. The biocompatible polymeric nanoparticles of claim 1, wherein the functional metal nanostructures comprise a mixture of gold (Au) nanorods and magnetic nanoparticles.

11. The biocompatible polymeric nanoparticles of claim 1, further comprising:
at least one active ingredient.

12. A process for preparing the biocompatible polymeric nanoparticles of claim 1, the process comprising:
preparing an emulsion comprising: (a) a hydrophobic phase comprising a solution of PHA in at least one organic solvent in which the functional metal nanostructures comprising gold (Au) nanostructures are dispersed; (b) an aqueous phase; and (c) at least one surfactant;
subjecting the emulsion to ultrasonic treatment; and
evaporating the at least one organic solvent from the emulsion after the ultrasonic treatment so as to obtain a suspension of the biocompatible polymeric nanoparticles which incorporates the functional metal nanostructures.

13. A process for preparing the biocompatible polymeric nanoparticles of claim 1, the process comprising:
preparing a solution of PHA in at least one organic solvent;
preparing a suspension of the functional metal nanostructures comprising gold (Au) nanostructures in an aqueous medium in a presence of at least one surfactant; and
contacting the solution of the PHA with the suspension of the functional metal nanostructures so as to obtain a suspension of the biocompatible polymeric nanoparticles which incorporates the functional metal nanostructures.

14. The biocompatible polymeric nanoparticles of claim 1, for use as a contrast agent in diagnostic image analysis.

15. The biocompatible polymeric nanoparticles of claim 1, for use in treatment of cancer.

16. The biocompatible polymeric nanoparticles of claim 14, wherein the diagnostic image analysis comprises magnetic resonance techniques or photoacoustic techniques.

17. The biocompatible polymeric nanoparticles of claim 6, wherein the gold nanorods have an average length greater than or equal to 10 nm and less than or equal to 100 nm.

18. The biocompatible polymeric nanoparticles of claim 6, wherein the gold nanorods have an average width greater than or equal to 2 nm and less than or equal to 25 nm.

19. The biocompatible polymeric nanoparticles of claim 6, wherein the gold nanorods have an aspect ratio, of length divided by width, greater than or equal to 2:1 and less than or equal to 20:1.

20. The biocompatible polymeric nanoparticles of claim 6, wherein the gold nanorods have an aspect ratio, of length divided by width, greater than or equal to 3:1 and less than or equal to 10:1.

* * * * *